Figure 1:
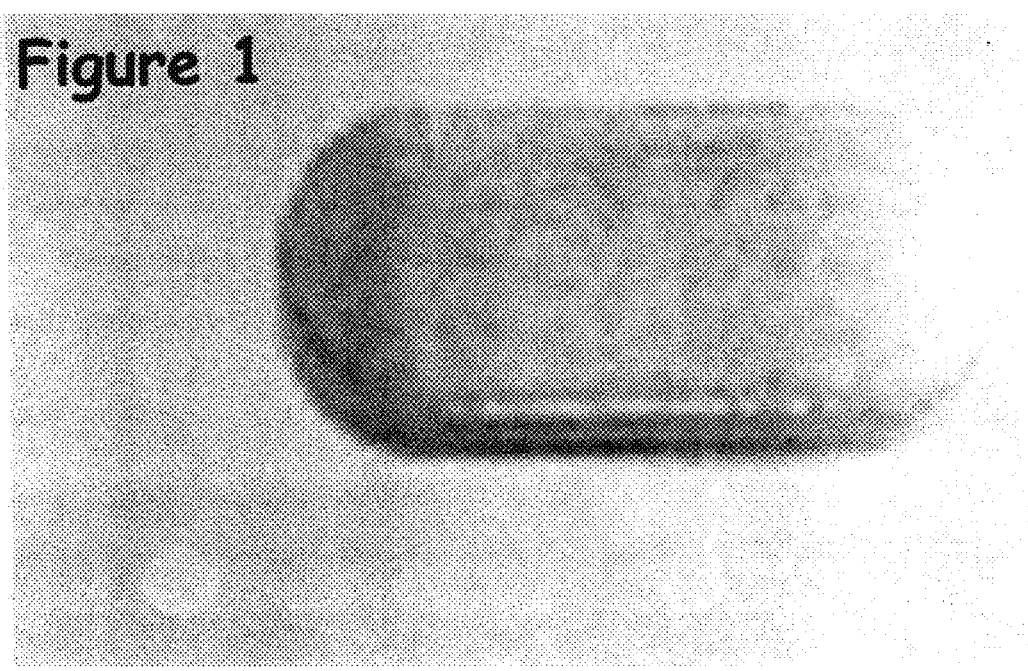

United States Patent [19]
Stevenot

[11] Patent Number: 6,143,300
[45] Date of Patent: Nov. 7, 2000

[54] FEM-EASE, A SUPPLEMENT FOR THE SYMPTOMS OF CYSTITIS, URINARY TRACT INFECTIONS AND PREMENSTRUAL SYNDROME

[75] Inventor: Robin Ann Stevenot, P.O. Box 578487, Modesto, Calif. 95357-8487

[73] Assignee: Robin Ann Stevenot, Northbend, Oreg.

[21] Appl. No.: 09/132,631

[22] Filed: Aug. 11, 1998

[51] Int. Cl.$^7$ .................................................. A01N 65/00
[52] U.S. Cl. ............................................................ 424/195.1
[58] Field of Search .......................................... 424/195.1

[56] References Cited

PUBLICATIONS www.hometownrx.com/docs/herbs (kava kava and dandelion root), Jul. 21, 1999.
www.lafemproducts.com, Jul. 21, 1999.

*Primary Examiner*—Herbert J. Lilling

[57] ABSTRACT

Over 450,000 women in the united states suffer from the medical disorder cystitis and several hundred in addition to this number, from urinary tract infections and premenstrual syndrome. Hundreds of clinical studies have shown the benefits of Kava Kava, Dandelion and L Arginine, each individually, as the relief for the many unpleasant symptoms that accompany cystitis, urinary tract infection and premenstrual syndrome. These beneficial results have been published in several prominent medical journals. Fem-Ease is a unique combination of all three ingredients together in one caplet. A light brown, cylinder shaped caplet with rounded corners, provides ease for the symptoms of cystitis, urinary tract infection and premenstrual syndrome. Two caplets in the morning and two caplets in the evening, provides a daily dose of 3000 mg of L Arginine, 790 mg of Kava Kava and 475 mg of Dandelion recommended to take at the first onset of symptoms.

17 Claims, 1 Drawing Sheet

FEM-EASE, A SUPPLEMENT FOR THE SYMPTOMS OF CYSTITIS, URINARY TRACT INFECTIONS AND PREMENSTRUAL SYNDROME

BACKGROUND

1. Field of Invention

This invention relates to an herbal and amino acid supplement designed to ease the discomfort of cystitis, urinary tract infection and premenstrual syndrome.

2. Description Prior Art

Medical doctors currently advise two types of treatments for cystitis: synthetic medications and surgery. Cystitis is inflammation of the bladder, usually occurring secondary to infections that involve associated organs (kidney, prostate, urethra). Lesion or ulcerative areas form in the lining of the bladder causing painful-frequent urination, abdominal pain, stress and severe depression. Cystitis sufferers find themselves frequenting the bathroom up to 60 times a day. The state of California provides permanent disability to women with long term documented histories of cystitis. Sufferers find themselves relying upon pain medications and antidepressants to get through the day. Work, relationships and normal daily activities become things of the past. Etiology of cystitis is still unknown. The four medications being used at this time to treat the symptoms of cystitis are Elmiron, DMSO, Hydroxyzine and Cystistat. These medications offer temporary relief but are not without side effects. Both DMSO and Cystistat are medications that need to be instilled into the bladder through means of catheterization. The user inserts a small flexible tube into the urethra and instills the medication into the bladder then holds it in as long as possible. Both of these medications attack the bacteria and free radical cells in the lining of the bladder then remove them as urination occurs. The method has been proven safe but with side effects. Those are: exacerbation of urinary frequency and urgency, odor, bladder irritation, bleeding of the gums and potential for increased infection during insertion of the catheter. The length of time the user holds the medication in, improves the benefits but is not worth the pain and discomfort. Treatment is 1–3 times a week for 2–4 months before symptoms begin to subside. Both Cystistat and DMSO are still in experimental stages. Medication costs are up to $200.00 per 4 installations a month plus $20.00 for FDA clearance fees. Additional treatments will cost up to $150.00 each. Elmiron and Hydroxyzine are two medications to be taken by mouth 1–3 times a day. Its is necessary to increase doses until adequate levels are reached in the body. This is estimated at 6–8 weeks. Elmiron has been shown to decrease the inflammation in the bladder wall reducing the symptoms of urination frequency and painful urination. Side effects may include hair loss, rash, head ache, swelling of the extremities, stomach upset and diarrhea. Hydroxyzine has been shown to decrease the histamine release in the body. Its benefits are unknown, yet cystitis sufferers have noticed some relief while taking this medication. Side effects are dry mouth, sedation, increased depression in patients diagnosed with concurrent depression and fetal abnormalities have been seen in animal studies. Medication costs are up to $160.00 for a one month supply. Taking these two drugs for eight weeks to four months may be required before reaching the maximum effect.

The two types of surgical procedures available at this time are Augmentation Cystoplasty and Urinary Diversions. Both surgical procedures are generally considered the treatment of last resort by cystitis sufferers and their doctors. The obvious reasons are that surgery is invasive and irreversible and many sufferers who choose to have surgery, do not improve. Both procedures have been proven to be painfull, debilitating and are considered drastic measures for relieving the discomfort of cystitis. In augmentation cystoplasty, part or most of the bladder is surgically removed and replaced with a section of the patients bowel, thus forming a new bladder. The new bladder stores and collects the urine but does not empty as the original bladder did by routine urination. The patient will need to catheterize themselves when urgency to urinate occurs. The patients willingness and ability to perform clean intermittent catheterization postoperatively, are critical to both long-term success of the procedure and patient satisfaction For example, if the bladder fills and is not emptied when sensation to urinate occurs, stretching of the bladder tissue and surgical site could cause a tear in the scar and a leakage of urine. Bowel tissue does not stretch like bladder tissue does. Repeat surgery is the only treatment to fix this leak. So holding it for a more convenient moment, is out of the question. Self catheterization, inserting a long soft plastic tubing into the urethra to allow for manual removal of urine, can take up to 30 minutes to perform. A clean surface to lay out all the supplies that are needed, is also necessary to prevent infection. Side effects are continued urinary frequency and urgency, repeat surgery due to tears in the surgical site, complete shut down of the bladder requiring a stoma to be placed in the patients abdomen where an outside bag is connected for urine collection, infection, bleeding and possibly no improvement at all from previous symptoms. Urinary diversions consist of three different types: Ileal conduit, ureterostomy and continent urinary diversion. Heal conduit involves taking a portion (6 to 8 inches) of the bowel and using one end of the section to create a opening in the abdomen. Then the ureters, the passage way for the urine to travel from the kidney to the bladder, are implanted into the piece of bowel bypassing the bladder and an external pouch is worn to collect the urine. This serves as a new passageway for the urine to flow to the outside of the abdomen. Continent Urinary diversion is a reservoir/pouch that collects and evacuates urine through a continent stoma or opening in the abdomen. It is constructed using various portions of the small and large intestine. The portion of the intestine is used to create a new bladder (reservoir) inside of the abdomen. Since the reservoir is internal, the patient need not wear an external pouch. The reservoir is catheterized at scheduled times to drain urine. It must be irrigated to maintain patency. This is done by instilling acidic sterile water into the new bladder on a daily basis. Once again, each of these procedures requires invasive surgery. Side effects are infection, bleeding and closure of the stoma requiring repeat surgery. Frequent catheterization is necessary and an inconvenience. Self image plays an important role in recovery by this procedure. Depression and anxiety have been documented during the 8–10 days of hospital stay post surgery. The patient is then medicated with antidepressants and counseling is recommended Urinary tract infections (UTI) have been treated for years with the antibiotics Bactrim, Macrodantin and a combination of Sulfa drugs that offer quick relief, but for those sufferers of chronic UTI's these same antibiotics after several prescriptions become useless as the body forms a resistance to them. Side effects of these antibiotics include, and are limited to, body rash, abdominal pain, nausea, headache, lupus, shock, kidney disease, liver disease, lung disease, insomnia, weakness and rare deaths. Urinary tract infections are caused by germs that invade the tract causing symptoms of frequent-urgent need to urinate, severe burning sensation upon urination, bloating or water retention and stress. Dietary changes and hygiene changes along with encouragement to drink 2000–3000 cc of water per day, that is twelve 8 oz glasses, leaves the sufferer full and visiting the bathroom too often to enjoy normal daily routines. UTI sufferers become dependent on pain relievers to alleviate the pain. Premenstrual Syndrome (PMS) is a combination of symptoms that for years have gone untreated. Symptoms occur a few days prior to onset of the menstrual cycle. Emotional unpredictability, depression, weight gain from fluid retention, breast tenderness and bouts of crying, anger and migraines headaches can be seen during this period. Over this past two decades, more attention has been focused on this condition. Antidepressant and mood elevators such as Prozac, Valium, Xanax, Elival, Zoloft and Effexor have been prescribed, more than any other class of medications in the USA, for the relief of symptoms. Yet most doctors will tell you this is a band-aid treatment. The side effects of these medications then requires additional medication. Side effects include but are not limited to, general malaise, insomnia, nervousness, dry mouth, headache, nausea, hallucinations, blurred vision, fast heart rate, chest pain and sexual dysfunction. The sufferers finds themselves lifeless and absent of normal emotions.

OBJECTS AND ADVANTAGES

Several objects and advantages of the present invention Fem-Ease are:

(a) to provide a supplement that is natural to the body (b) to provide a supplement that will allow women to live a normal life without the need for disability (c) to provide a supplement without side effects, that are worse than and that will intensify the existing symptoms.

(d) to provide a supplement that eases symptoms naturally without the need for radical surgical procedures (e) to provide a supplement that prevents women from dreading those few days prior to menses (f) to provide a supplement that doesn't require a costly doctor bill and expensive procedures (g) to provide a supplement that is safe, inexpensive, easy to swallow and can be easily purchased These advantages of Fem-Ease are achieved by three ingredients: 1 arginine, kava kava and dandelion 1. L arginine is an amino acid found in all protein rich foods. Arginine is stored in every muscle in the human body. Over the past 9 years, it has been studied in hundreds of clinical research studies for its use in the cardiac, respiratory, wound repair, sexuality and recently urology fields, yielding over 3000 papers a year. Studies show that 1 arginine changes the oxygen molecule in the body into nitric oxide. Nitric oxide is a gas that stimulates mast cells. Mast cells repair connective tissue by enriching its blood supply as well as delivering histamines. Histamines are responsible for repairing injured tissue. The lining of the connective tissue is called the epithelial lining. This is the lining found inside the bladder. It is in this lining that the lesions or ulcers occur with cystitis. The break down of this lining causes reduced blood supply and dead areas. These areas in turn become ulcerative. The bacteria in the bladder can irritate these areas even more. Why this lining breaks down and reduced blood supply occurs, is unknown. Increasing the amount of 1 arginine in the body in turns increases the amount of mast cells. In greater quantities, these cells prevent the break down of the epithelial lining and prevent the ulcers or lesion from developing. Mast cells restore health to the existing ulcerative areas. Fem-Ease provides the addition amount of 1 arginine needed to achieve this benefit.

2. Kava kava is an herb which root is ground into powder form and used as an anti-anxiety and antiinflammatory. Several clinical studies have shown it to be parallel in its effect to xanax and valium without the undesirable side effects. It reduces inflammation, stress and discomfort associated with urinary tract infection and premenstrual syndrome. It is an herb described as leaving the consumer feeling relaxed, peaceful, content with a sharpening of the senses. A calmness overcomes the body and clarity in thought patterns replaces pain, stress and anxiety. Normal daily activities can be resumed. It has been used for centuries by many founders in this country and abroad for its stress and anxiety relieving properties.

3. Dandelion is an herb which leaves are dried and used as a diuretic to reduce water retention and bloating. It is full of vitamin Bs and vitamin A. Both provide essential nutrition to every living cell in the body. Cells require vitamin B and A to provide health to all living tissue. It is also one of the best sources of potassium, replacing that which is flushed from the body when a diuretic is used. It thus makes an ideally balanced diuretic that may be used safely wherever such an action is needed, such as in cases of water retention due to cystitis and premenstrual syndrome.

DRAWING FIGURE

In the picture, a caplet of Fem-Ease is shown in magnified view.

FIG. 1 shows a brownish colored caplet with a cylinder shape and rounded corners.

DESCRIPTION

Serving size contains 4 caplets with:

(a) 3000 mg of 1 arginine (b) 790 mg of kava kava (c) 475 mg of dandelion

Each caplet is in a cylinder shape with rounded corners. It is light brown in appearance. Each caplet measures 6 mm×8 mm×21 mm long in actual size. It is shinny in appearance due to a light coating for easy to swallowing. Fem-Ease comes in a hard plastic white bottle with a factory sealed screw on lid. Each bottle contains 90 caplets. It is recommended that Fem-Ease be taken 2 caplets in the morning and 2 caplets in the evening at the onset of symptoms.

CONCLUSION

Accordingly the reader will see that Fem-Ease can be taken safely without the unpleasant side effects and fear of radical surgical procedures.

Its provides reduction of ulceration's in the bladder wall

It promotes health to the lining of the bladder

Its provides ease to anxiety and stress

It prevents bloating and water retention

It provides essential nutrients to every living cell

It provides ease to emotional unpredictability.

I claim:

1. A supplement composition comprising the following ingredients:

a) L arginine, b) kava kava root, c) dandelion leaves, which supplement composition is an effective amount to relieve the symptoms of interstitial cystitis, urinary tract infection and premenstrual syndrome whereby the kava kava is the root which eases or reduces anxiety or inflammation and the dandelion leaves acts as a diuretic to reduce water retention and bloating.

2. The supplement composition of claim 1 consisting essentially of the following ingredients:
   a) L arginine,
   b) kava kava root,
   c) dandelion leaves.

3. The supplement composition of claim 1 consisting of the following ingredients:
   a) L arginine,
   b) kava kava root
   c) dandelion leaves.

4. The supplement composition of claim 1 comprising the following ingredients:
   a) about 70.34% L arginine,
   b) about 18.52% Kava kava root
   c) about 11.14% dandelion leaves.

5. The supplement composition of claim 1 consisting essentially of the following ingredients:
   a) about 70.34% L arginine,
   b) about 18.52% kava kava root,
   c) about 11.14% dandelion leaves.

6. The supplement composition of claim 1 consisting of the following ingredients:
   a) about 70.34% L arginine,
   b) about 18.52% kava kava root
   c) about 11.14% dandelion leaves.

7. A caplet having the supplement composition of any one of claims 1–3.

8. A caplet having the supplement composition of claim 1 comprising about 70.43% of L arginine.

9. A caplet having the supplement composition of claim 1 comprising about 18.52% kava kava root.

10. A caplet having the supplement composition of claim 1 comprising about 11.14% dandelion laves.

11. A method for treating a patient for relieving the symptoms of interstitial cystitis by administering an effective amount of the supplement composition of any one of claims 1–3.

12. The method of claim 11 whereby the supplement composition is in the form of a caplet.

13. A method for treating a patient for relieving the symptoms of urinary tract infections by administering an effective amount of the suppliment composition of any one of claims 1–3.

14. The method of claim 13 whereby the supplement composition is in the form of a caplet.

15. A method for treating a patient for relieving the symptoms of premenstrual syndrome by administering an effective amount of the supplement composition of any one of claims 1–3.

16. The method of claim 15 whereby the supplement composition is in the form of a caplet.

17. The caplet of claim 7 containing 3000 mg of L arginine, 790 mg of kava kava root and 475 mg of dandelion leaves.

* * * * *